United States Patent
Bronkalla et al.

(10) Patent No.: US 10,783,633 B2
(45) Date of Patent: Sep. 22, 2020

(54) AUTOMATICALLY LINKING ENTRIES IN A MEDICAL IMAGE REPORT TO AN IMAGE

(71) Applicant: INTERNATIONAL BUSINESS MACHINES CORPORATION, Armonk, NY (US)

(72) Inventors: Mark D. Bronkalla, Waukesha, WI (US); Rebecca Trunnell-Hyman, Wildwood, MO (US); Prasanth Prasanna, Salem, OR (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 184 days.

(21) Appl. No.: 15/962,724

(22) Filed: Apr. 25, 2018

(65) Prior Publication Data
US 2019/0333217 A1    Oct. 31, 2019

(51) Int. Cl.
*G06K 9/00* (2006.01)
*G06T 7/00* (2017.01)
(Continued)

(52) U.S. Cl.
CPC ............ *G06T 7/0014* (2013.01); *G06T 7/174* (2017.01); *G06T 11/60* (2013.01); *G16H 30/20* (2018.01);
(Continued)

(58) Field of Classification Search
CPC ....... G06T 7/0014; G06T 7/174; G06T 11/60; G06T 2207/30004; G16H 30/20; G16H 50/70; G16H 30/40
(Continued)

(56) References Cited

U.S. PATENT DOCUMENTS

| 8,935,155 B2 | 1/2015 | Bretschneider et al. |
| 2003/0105638 A1 | 6/2003 | Taira |

(Continued)

FOREIGN PATENT DOCUMENTS

WO    2011/132097 A2    10/2011

OTHER PUBLICATIONS

U.S. Appl. No. 15/962,724, filed Apr. 25, 2018.
(Continued)

*Primary Examiner* — Van D Huynh
(74) *Attorney, Agent, or Firm* — Michael Best & Friedrich LLP (57) ABSTRACT

Methods and systems for automatically linking entries in a medical image report to an image of a medical image study. One method includes identifying a first plurality of image features referenced in text included in the medical image report using natural language processing, identifying a second plurality of image features in images included in the medical image study, and comparing the first plurality of image features and the second plurality of image features. In response to a first image feature included in the first plurality of image features and a second image feature included in the second plurality of image features matching, the method includes creating a data link between the medical image report and an image included in the medical image study including the second image feature, and automatically inserting the data link into the medical image report, the data link selectable by a user to display the image.

18 Claims, 2 Drawing Sheets

(51) Int. Cl.
*G16H 50/70* (2018.01)
*G06T 11/60* (2006.01)
*G06T 7/174* (2017.01)
*G16H 30/20* (2018.01)

(52) U.S. Cl.
CPC ... *G16H 50/70* (2018.01); *G06T 2207/30004* (2013.01)

(58) Field of Classification Search
USPC .......................................................... 382/128
See application file for complete search history.

(56) References Cited

U.S. PATENT DOCUMENTS

| | | | | |
|---|---|---|---|---|
| 2006/0271403 | A1* | 11/2006 | Iwasa | G06Q 10/10 705/2 |
| 2008/0247676 | A1* | 10/2008 | Minakuchi | G16H 15/00 382/305 |
| 2011/0075901 | A1* | 3/2011 | Nakamura | G16H 15/00 382/128 |
| 2012/0035963 | A1 | 2/2012 | Qian et al. | |
| 2012/0131436 | A1* | 5/2012 | Leontiev | G16H 30/20 715/233 |
| 2014/0006926 | A1* | 1/2014 | Yeluri | G06F 19/321 715/234 |
| 2014/0316770 | A1* | 10/2014 | Sevenster | G06F 40/10 704/9 |
| 2015/0032471 | A1* | 1/2015 | Arazi | G06F 19/321 705/3 |
| 2016/0314278 | A1* | 10/2016 | Mabotuwana | G06F 40/279 |
| 2017/0337328 | A1* | 11/2017 | Ruppertshofen | G06F 19/00 |

OTHER PUBLICATIONS

U.S. Appl. No. 15/962,731, filed Apr. 25, 2018.
Shin et al., "Interleaved Text/Image Deep Mining on a Large-Scale Radiology Database for Automated Image Interpretation," Journal of Machine Learning Research, 2016, 17:1-31.
Non-Final Office Action from the U.S. Appl. No. 15/962,731 dated Nov. 18, 2019 (8 pages).
Notice of Allowance from the U.S. Appl. No. 15/962,731 dated Feb. 12, 2020 (7 pages).

* cited by examiner

AUTOMATICALLY LINKING ENTRIES IN A MEDICAL IMAGE REPORT TO AN IMAGE

FIELD

Embodiments described here relate to methods and systems for automatically linking entries in a medical image report to one or more images of a medical image study.

SUMMARY

When viewing a report for a medical image study, a physician viewing the report (a "reading physician") may desire to view the images that correspond to a particular finding or statement in the report. However, although the report may be displayed within an image viewer, navigating to the desired images is a manual process that may take an extended period of time, especially when a large number of images were taken for a particular image study. Furthermore, although some reading physicians may include a reference number or identifier for an image that supports a particular finding or statement, this process is error-prone and relies on a reading physician to manually add such a reference. Similarly, most reports are plain text (delivered by HL7), which eliminates the ability to store images in the report and any embedded links actually impede the readability and formatting of the report. Additionally, to be compatible with an image viewer, embedded links use absolute rather than relative references so that the viewers can be launched with the full uniform resource locator (URL) context from the report. In many cases the images and the associated report are sent to a different facility for review. Therefore, absolute links are broken since the image storage system may be inaccessible by the report viewer, which may receive image reports via compact disc (CD) or image sharing. Thus, currently there is no automated means for providing links between a report and the images the report references.

Accordingly, embodiments described herein provide methods and systems for automatically linking entries in a medical image report to an image of a medical image study. For example, when a report is received, the report is processed via natural language processing (NLP) to extract image features (anatomical structures, descriptions of pathology, user artifacts, medical structures, and the like), which can be compared with image features extracted from one or more images of the image study associated with the report. The image features may be extracted from the images using an anatomical atlas, descriptions of pathology, image segmentation, or the like. The image features extracted from the report may be based on report sub-headings or from within the body of text included in the report. Hyperlinks can then be inserted into the report when an image feature extracted from an image corresponds to an image feature extracted from the report. When the inserted hyperlink is selected, the corresponding image including the matching image feature can be displayed. A similar hyperlink can be inserted (visibly or invisibly overlaid) on the image, so that a user can select the hyperlink while viewing the image to view the corresponding report and, in particular, the corresponding portion, finding, or statement included in the report or additionally to the "prior" comparison studies with or without the item of interest such as an implanted device or lesion. In some embodiments, link insertion may be performed by the viewing system using an already distributed report, which allows the report links to be relative within the viewing system.

For example, one embodiment provides a method for automatically linking entries in a medical image report to at least one image of a medical image study. The method includes identifying, with at least one electronic processor, a first plurality of image features referenced in text included in the medical image report using natural language processing and identifying, with the at least one electronic processor, a second plurality of image features in images included in the medical image study. The method also includes comparing, with the at least one electronic processor, the first plurality of image features and the second plurality of image features. In response to a first image feature included in the first plurality of image features and a second image feature included in the second plurality of image features matching, the method includes creating, with the at least one electronic processor, a data link between the medical image report and an image included in the medical image study including the second image feature, and automatically inserting, with the at least one electronic processor, the data link into the medical image report, the data link being selectable by a user to display the image.

Another embodiment provides a system for automatically linking entries in a medical image report to at least one image of a medical image study. The system includes at least one electronic processor. The at least one electronic processor is configured to identify a first plurality of image features referenced in text included in the medical image report using natural language processing, identify a second plurality of image features in images included in the medical image study, and compare the first plurality of image features and the second plurality of image features. In response to a first image feature included in the first plurality of image features and a second image feature included in the second plurality of image features matching, the at least one electronic processor is further configured to create a data link between the medical image report and an image included in the medical image study including the second image feature, and automatically insert the data link into the image, wherein the data link is selectable to display the medical image report.

Yet another embodiment provides non-transitory, computer-readable medium storing instructions that, when executed by at least one electronic processor, cause the at least one electronic processor to perform a set of functions. The set of functions includes identifying a first plurality of annotations referenced in text included in a medical image report using natural language processing, identifying a second plurality of annotations in images included in a medical image study associated with the medical image report, and comparing the first plurality of annotations and the second plurality of annotations. In response to a first annotation included in the first plurality of annotations and a second annotation included in the second plurality of annotations matching, the set of functions also includes creating a data link between the medical image report an image included in the medical image study including the second annotation, and inserting the data link into the medical image report, the data link selectable to display the image.

A further embodiment provides a method for automatically linking entries in a medical image report to an image of at least one medical image study. This method includes identifying, with at least one electronic processor, a description of pathology in text included in the medical image report using natural language processing and applying, with the at least one electronic processor, a model to select for the medical image report at least one modality and at least one image included in the at least one medical image study generated by the at least one modality. The method also includes creating, with the at least one electronic processor, a data link between the description of pathology and the at least one image included in the at least one medical image study generated by the at least one modality, and automatically inserting, with the at least one electronic processor, the data link into the medical image report, the data link being selectable by a user to display the at least one image included in the at least one image generated by the at least one modality.

Similarly, another embodiment provides a system for automatically linking entries in a medical image report to an image of at least one medical image study. The system includes at least one electronic processor. The at least one electronic processor is configured to identify a description of pathology in text included in the medical image report using natural language processing and apply a model to select for the medical image report at least one modality and at least one image included in the at least one medical image study generated by the at least one modality. The at least one electronic processor is also configured to create a data link between the description of pathology and the at least one image included in the at least one medical image study generated by the at least one modality, and automatically insert the data link into the medical image report, the data link being selectable by a user to display the at least one image included in the at least one image generated by the at least one modality.

In addition, an embodiment described herein provides non-transitory, computer-readable medium storing instructions that, when executed by at least one electronic processor, cause the at least one electronic processor to perform a set of functions. The set of functions includes identifying a description of pathology in text included in a medical image report using natural language processing and applying a model to select for the medical image report at least one modality and at least one image included in the at least one medical image study generated by the at least one modality. The set of functions also includes creating a data link between the description of pathology and the at least one image included in the at least one medical image study generated by the at least one modality, and automatically inserting the data link into the medical image report, the data link being selectable by a user to display the at least one image included in the at least one image generated by the at least one modality.

Other aspects of the invention will become apparent by consideration of the detailed description and accompanying drawings and appendices.

DETAILED DESCRIPTION

Before any embodiments are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. Also, electronic communications and notifications may be performed using any known means including secure email, direct connections, wired connections, wireless connections, etc. It should also be noted that a plurality of hardware- and software-based devices, as well as a plurality of different structural components may be utilized to implement the invention. Furthermore, and as described in subsequent paragraphs, the specific configurations illustrated in the drawings are intended to exemplify embodiments of the invention, it being understood that other alternative configurations are possible.

It should also be noted that embodiments described herein may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processing units. As such, and by way of example, "electronic devices," "computers," "computing devices," "controllers," "control devices," or "control modules" described in the present specification can include one or more processing units, one or more computer-readable medium modules, one or more input/output interfaces, and various connections (e.g., a system bus) connecting the components.

Figure 1:
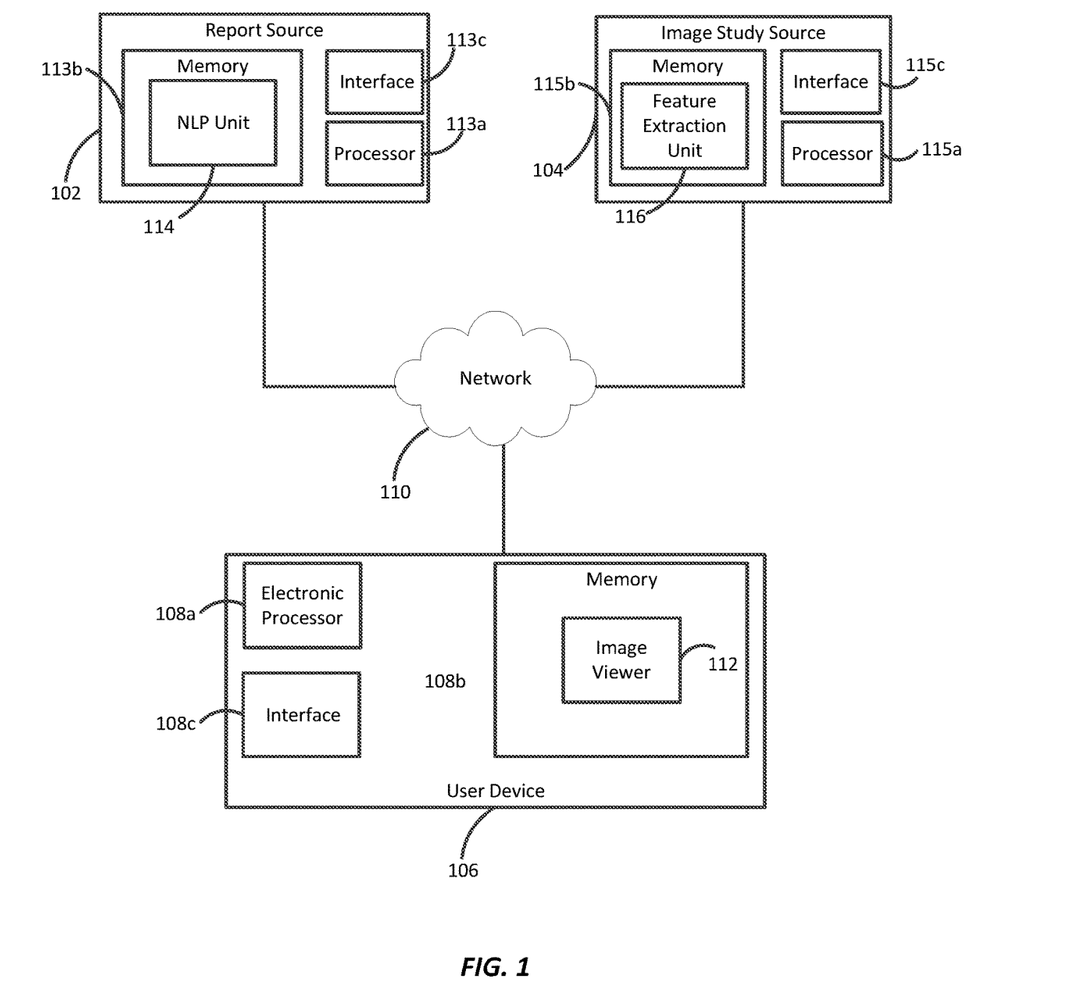
FIG. 1 illustrates a medical imaging system according to one embodiment.

FIG. 1 illustrates a medical imaging system 100. The system 100 includes a report source 102, an image study source 104, and a user device 106. It should be understood that the system 100 may include additional components than those illustrated in FIG. 1. For example, the system 100 may include a plurality of user devices 106 although only one is illustrated in FIG. 1. Also, in some embodiments, the system 100 includes multiple report sources 102, multiple image study sources 104, or a combination thereof. The system 100 may also include one or more imaging modalities that generate one or more images associated with one or more types of medical imaging procedures. Furthermore, in some embodiments, the functionality provided by the report source 102 can be combined with the functionality of the image study source 104 in a single device.

The image study source 104 includes one or more databases that store medical image studies generated by one or more imaging modalities. In some embodiments, the image study source 104 includes a picture archiving and communication system ("PACS"), a cloud storage system, or the like.

The report source 102 stores image reports. An image report includes findings by a reading physician based on a set of images (an image study) generated during a medical imaging procedure. In some embodiments, the report source 102 includes a radiology information system ("RIS"). In other embodiments, the report source 102 can include a picture archiving and communication system ("PACS"), an electronic medical record ("EMR") system, a dictation system, a cloud storage system, a hospital information system ("HIS"), or the like. In some embodiments, the report source 102 is operated by the same entity that operates the image study source 104. However, in other embodiments, the report source 102 and the image study source 104 are operated by different entities. Also, in some embodiments, the image study source 104 is included in the report source 102.

The user device 106 is an electronic device operated by an end user, such as a physician, a caretaker, an assistant, a patient, or the like, to view a medical image report. The user device 106 may be a workstation, a personal computer, a laptop, a tablet computer, a smartphone, a smart watch or other wearable, a smart television, or the like.

As illustrated in FIG. 1, the user device 106 includes an electronic processor 108a, a computer-readable memory module 108b, and a communication interface 108c. The memory module 108b can include non-transitory memory, such as random access memory, read-only memory, or a combination thereof. The electronic processor 108a can include a microprocessor configured to execute instructions stored in the memory module 108b. The memory module 108b can also store data used with and generated by execution of the instructions. The communication interface 108c allow the user device 106 to communicate with external devices, including one or more wired or wireless networks 110 (for example, the Internet, a clinical messaging network, a local area network, or the like) that also communicate with the report source 102, the image study source 104, or a combination thereof. It should be understood that the user device 106 may include additional components than those listed in FIG. 1 in various configurations. For example, in some embodiments, the user device 106 includes a plurality of electronic processors, memory modules, communication interfaces, or a combination thereof.

As also illustrated in FIG. 1, the memory module 108b may store an image viewer 112. The image viewer 112, as executed by the electronic processor 108a, allows a user to access stored images and stored reports. In some embodiments, image viewer 112 includes a browser application configured to access a web page for accessing the report source 102, the image study source 104, or a combination thereof. In other embodiments, however, the image viewer 112 is a dedicated application for accessing the report source 102, the image study source 104, or a combination thereof.

As illustrated in FIG. 1, the report source 102 and the image study source 104 may include similar components as the user device 106. For example, the report source 102 and the image study source 104 may each include one or more servers that each include an electronic processor 113a and 115a, a computer-readable memory module 113b and 115b, and an communication interface 113c and 115c similar to the electronic processor 108a, memory module 108b, and communication interface 108c described above with respect to the user device 106. Again, it should be understood that the report source 102 and the image study source 104 may include additional components than those listed in FIG. 1 in various configurations. For example, in some embodiments, the report source 102, the image study source 104, or a combination thereof includes a plurality of electronic processors, memory modules, communication interfaces, or a combination thereof.

As illustrated in FIG. 1, the report source 102 includes (stored within the memory module 113b) a natural language processing ("NLP") unit 114. In one embodiment, the NLP unit 114 is a software program including instructions for processing natural language (textual language) included in a medical image report. For example, the NLP unit 114 processes text included in medical image reports to identify particular keywords, including, for example, image features such as medical features (for example, organs, organ function or other descriptions of pathology, medical devices or implants, and the like) and user artifacts (for example, measurements or observations). The extracted features may be mapped to a general ontology such as, for example, UMLS (Unified Medical Language System—Metathesaurus by US National Library of Medicine), SNOMED-CT (Systematized Nomenclature of Medicine-Clinical Terms), as well as common hierarchies and synonyms for various features of the extracted features. For example, a hip implant may be referred to as the hip prosthesis with sub-components, such as acetabular cup, femoral head or ball, and stem and any of these subcomponents could be key words for the detected image components.

Similarly, the image study source 104 includes (stored within the memory module 115b) a feature extraction unit 116. In one embodiment, the feature extraction unit 116 is a software program including instructions identifying features in an image, such as anatomical structures or views, such as Parasternal Long Axis that contains several different anatomical structures. In some embodiments, the feature extraction unit 116 identifies image feature using image segmentation. Image segmentation is a process of partitioning a digital image into multiple segments (sets of pixels) to locate objects and boundaries in images. For example, the feature extraction unit 116 may be configured to process an image and determine anatomical localization information using one or more anatomical atlases or from a different localization or recognition approach, such as, for example, a neural network recognition approach. For example, in a chest computed tomography ("CT") image, anatomical regions, such as the ascending aorta, left ventricle, T3 vertebra, and other regions, can be identified and labeled, such as by using multi-atlas segmentation. Each atlas includes a medical image obtained with a known imaging modality and using a particular imaging procedure and technique wherein each pixel in the medical image is labeled as a particular anatomical structure. Accordingly, an atlas can be used to label anatomical structures in an image.

After processing an image, the feature extraction unit 116 may output a table of extracted image features. The table lists features (anatomical structures, descriptions of pathology, and the like as described above) detected in a set of images or image volume and identifiers of the images or frames that reference each feature. For example, the liver in an abdominal CT study may be seen in series 3 images 200-240, but for an MR study the liver may be seen in series 1 images 5-10, 20-24, 40-43 as it may be visible in multiple planes of the MR acquisition series. Similarly, in an echocardiography study, the left ventricle (LV) may be present in multiple views (2 chamber, 4 chamber, and the like) so the LV may have 6-10 references in multiple motion images (for example, image 3 frames 45-70, image 7 frames 65-80, and the like) and single frame captures as commonly done for measurements.

It should be understood that the table of features is not limited to anatomical structures. For example, in some embodiments, the feature extraction unit 116 is configured to recognize implanted devices (for example, artificial hip acetabular implant, vena cava filter, or PICC line) in an image and include references for these devices in the table. The mechanism for the extraction of non-anatomical features may use an entirely disparate mechanism from what is used for the identification of the anatomical features. An example of such an object classifier, detector is the IBM Watson Power AI Vision system. However it is also advantageous to use the anatomical location to inform detected device choices and speed the matching process. Also, in some embodiments, the feature extraction unit 116 is configured to extract measurements that have been performed and added to the images either as part of the pixel data or as a presentation state reference. For example, with ultrasound images it is common for the sonographer to make a number of measurements during the exam and these measurements are often saved as image screen shots. These measurements can be further enhanced by using the registration processes used in the anatomical localization processes described above to match the screen short with the measurement to the frame of the multi-frame acquisition or series (ultrasound image movie). Accordingly, a user could use the table generated by the feature extraction unit 116 to find both the measurement screen shot and the original sequence, which can be displayed to assess the accuracy of the measurement.

It should be understood that the functionality described herein as being performed by the NLP unit 114 and the feature extraction unit 116 may be distributed and combined in various configurations. For example, in some embodiments, the functionality provided by NLP unit 114, the feature extract unit 116, or both may distributed among multiple modules or software units. Also, in some embodiments, the NLP unit 114 and the feature extraction unit 116 may both be included in the report source 102 or the image study source 104. Furthermore, in some embodiments, the NLP unit 114, the feature extraction unit 116, or both may be included in the user device 106. Similarly, in some embodiments, the NLP unit 114, the feature extraction unit 116, or both are included in one or more other devices configured to process images and reports as described herein. For example, in some embodiments, a server may be configured to access reports stored in the report source 102 and access images stored in the image study source 104 and perform the feature extraction and natural language processing as described herein. Additionally, the NLP feature extraction is not limited to radiology or cardiology reports but is equally applicable to clinical visit notes or surgical notes especially as the surgical specialists often read their own imaging studies, refer to image features during a visit or discussion with a patient, or detail the surgical implant or removal of a device all of which can be image correlated.

Figure 2:
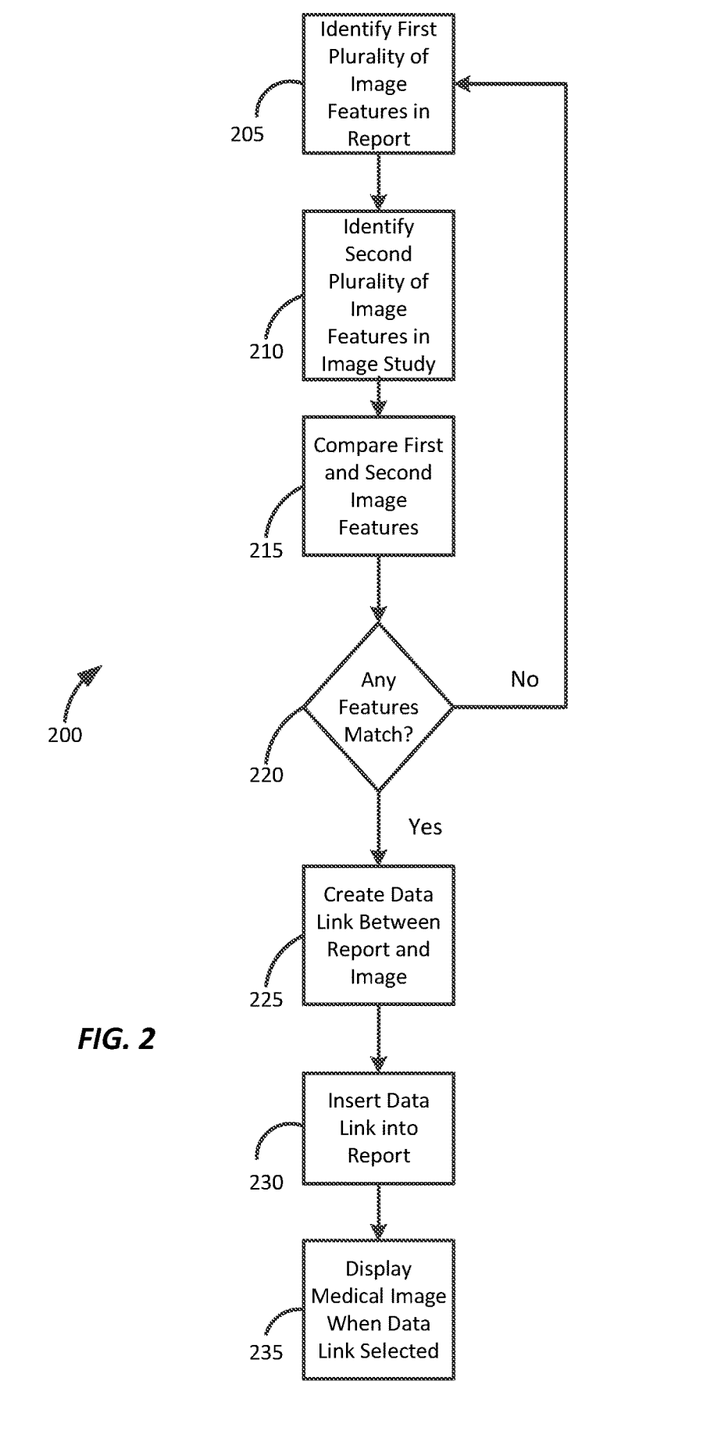
FIG. 2 illustrates a method of automatically linking entries in a document to images according to one embodiment.

FIG. 2 illustrates a method 200 of automatically linking entries in a report to images according to one embodiment. The method 200 is described as being performed by the report source 102, the image study source 104, or a combination thereof. For example, portions of the method 200 may be performed by the NLP unit 114 and the feature extraction unit 116 (as executed by an electronic processor 113a, the electronic processor 115a, or a combination thereof). However, as noted above, in some embodiments, all or a portion of the method 200 may be performed by the user device 106 or other devices with access to reports and associated images.

As illustrated in FIG. 2, the method 200 includes identifying (for example, using the electronic processor 113a of the report source 102), a first plurality of image features referenced in text included in the medical image report using the NLP unit 114 (at block 205). The image features may include medical structures, user artifacts, or a combination thereof. Medical structures may be anatomical structures (for example, a bone, an organ, a mass or tumor, a ligament, a muscle, and the like), surgical features (for example, an incision, sutures, and the like), medical devices (for example, a pacemaker, a metal rod or pin, a stent, and the like), or medical implants (for example, a device to replace a missing biological structure or descriptions of pathology, such as atrial fibrillation). Medical structures may also include imaging procedures or parameters, such as "pre-contrast" or "post-contrast." User artifacts may be measurements, annotations (graphical markings), qualitative values, labels, observations, captions, or other items added to an image by a user (or a computer as part of an automated analysis of an image). User artifacts may include specific references such as "suspicious lesion of the liver." Similarly, a user artifact may include a reference to a particular key image or presentation state.

The NLP unit 114 may be configured to store data regarding the identified first plurality of image features in a data structure such as a table. For example, when a physician prepares a medical image report, the physician uses terms to describe image features, including medical structures and user artifacts. The electronic processor 113a, using the NLP unit 114, processes text inserted into a report to detect such terms. The NLP unit 114 may be configured to store these detected terms (referencing image features) in the table along with data identifying one or more locations within the report including the detected term (or associated terms). The locations may include page numbers, line numbers, section numbers, or the like. The NLP unit 114 may be configured process text included in a body of the report. However, alternatively to in addition, the NLP unit 114 may be configured to use a format or structure of a report to identify the first plurality of medical structures. For example, the medical image report may process report subsections or headings for individual body parts, anatomical systems, types of images, and the like. The electronic processor 113a, using the NLP unit 114, may utilize the subsection names to quickly identify relevant terms used in the subsection. For example, the NLP unit 114 may determine that a subsection is named "Spine" and will look for language related to the spine in the subsection, such as "vertebra" or a specific structure or grouping (e.g. L5-S1 or sacrum, which is composed of multiple vertebrae or sub feature such as the right transverse process or spinous process of L3).

For some anatomical locations and devices there are a number of synonyms or acronyms (for example, "RCA" vs "Right Coronary Artery") and the NLP unit 114 may be configured to resolve these synonyms and acronyms and map these terms to supported anatomical locations or devices (locations or devices identified by the feature extraction unit 116 as described below). Additionally there may be greater or lesser specificity in the text than is supported in the anatomical localization performed by the feature extraction unit 116. For example, "Aortic Arch" may be mentioned in a report but the feature extraction unit 116 may be configured to perform anatomical localization to identify "ascending aorta" and "descending aorta" but not "aortic arch" or "aorta". Additionally, in the case of devices the feature processor may be able to recognize sub-components (e.g., acetabular cup vs femoral head vs stem) in a hip implant prosthesis. Accordingly, the NLP unit 114 may be configured to compare and map identified image features from a report to known features that may be extracted by the feature extraction unit 116. In some embodiments, to apply finer gradations, the NLP unit 114 may add additional layers of subdivisions to the atlas segmentation or subsequently apply additional rules to enable finer subdivisions (for example, proximal, mid, distal segments of bone or vessels, medial or lateral aspect/side of a structure, or superior vs inferior aspect).

As illustrated in FIG. 2, the method 200 also includes identifying (for example, with the electronic processor 115a) a second plurality of image features in images included in an image study associated with the medical image report via the feature extraction unit 116 (at block 210). The image study may be associated with the medical image by a unique identifier of the image study included in the image report. In other embodiments, information included in the report, such as patient, procedure date, and the like, may be used to identify the associated image study. The feature extraction unit 116 may be configured to analyze pixels in one or more images included in the image study to identify the second plurality of image features structures. For example, as described above, the feature extraction unit 116 may be configured to use image segmentation to identify anatomical structures in an image. The feature extraction unit 116 may also be configured to process metadata (such as header information) of an image to identify an image feature, such as user artifacts. Similar to the NLP unit 114, the feature extraction unit 116 may be configured to store identified image features in a data structure, such as a table. The table may include the identified features and a reference to a particular image, frame, or portion including the identified feature.

The method 200 also includes comparing the first plurality of image features and the second plurality of image features (at block 215) to determine if any features in the first plurality of image features and the second plurality of image features match. For example, the first plurality of image features may include a medical structure identified as a "liver," and the second plurality of image features may include a medical structure identified as a "liver." It should be understood that identified image features may "match" when they are identical or related. For example, when the first plurality of image features includes a "marked tumor" and the second plurality of image features include a graphical annotation marking a portion of an image, these features may be considered "matching." Similarly, when the first plurality of image features includes a "cranium" and the second plurality of image features includes a "skull," these features may be considered "matching" even though they are not identical. The use of an ontology or other hierarchical organization where the features identified in the report and the features identified in the images enables the resolution of differing levels of specificity found in the text or images. This is especially notable when a sub structure of either the anatomy (e.g. vertebral facet) or device (acetabular cup) or specific sub structures of the brain which are finer in granularity than may be supported in the anatomical localization or segmentation is mentioned in the report. Furthermore, additional location modifiers may be used with a given structure to add finer location information such as the distal portion of the femur, medial portion of the right side of the mandible can provide hints as to the best slices or views to use where a portion of the anatomy covers multiple images or slices. The modifiers discovered in the report are not limited to physical location but may also include other characteristics. For example, an "enhancing" lesion indicates that this was seen in the series that was taken after the addition of a contrast medium (e.g., iodinated contrast for CT, gadolinium for MR or other) and in the case of a study with both non-contrast and contrast series, the contrast series may be linked to the "enhancing" lesion mention in the report rather than the non-contrast series or study.

In response to the first plurality of image features and the second plurality of image features not including any matching features ("No" at block 220), the method 200 may consider other images included in image study or, if all of the images have been processed, return to waiting for a new medical image report and a new medical image to identify features within (such as at blocks 205 and 210, respectively).

Alternatively, in response to the first plurality of image features and the second plurality of image features including a matching feature ("Yes" at block 220), a data link is created between the medical image report and at least one image (at block 225) and is inserted into the medical image report (at block 230). The data link may be inserted at a location of the matching image feature, such as a matching medical structure. For example, if both the report and an image in the associated image study reference a "liver," a data link to an image and the structure or coordinates illustrating a liver may be inserted into the report, such as in a subsection of the report relating to the liver. The insertion of these data links may be especially useful to a lay person or referring physician who may not be adept at discerning the various structures especially in cross-sectional anatomy, such as, for example, CT or MR. For example, in the above example of a "liver," the right image or image view may be selected but optionally a highlight of the liver, such as an outline around the liver (displayed statically or momentary, such as displayed for three seconds and then disappeared). In some embodiments, the anatomy may also be shown in multiple views whether these views were present in the original study. For example, with reference to L3 a user may be interested in viewing both the axial view and the sagittal view simultaneously.

The data link (for example, a uniform resource locator ("URL")) identifies the medical image associated with the medical image report. Accordingly, the data link is selectable (for example, by a user of the user device 106 clicking on the data link) to view the medical image. The data link may be inserted in the medical report approximate to the matching feature. Thus, as a user reviews the report, the user can quickly access an image supporting or associated with a particular finding or statement in the report. Thus, by creating the data link when the medical image report and the at least one medical image contain the same image feature (for example, medical structure), the user can quickly select the data link to access and view the medical image (or portion of the medical image), which improves workflow, prevent errors, and limits wasted computer resources associated with manually attempting to identify a relevant image to a portion of a report.

The data link may be inserted in to the report as a standalone link. However, in other embodiments, the data link may be inserted or added to existing text in the report. For example, if a mass is described in a subsection of the medical image report, the electronic processor 108a may select the specific sentence or subsection that describes the mass and insert the data link into the sentence or subsection (by adding the data link as selectable text or by creating a hyperlink over existing text in the medical image report). Also, in some embodiments, the hyperlinks may be summarized in a table inserted into the report, which serves as a summary of the images linked with the report. Accordingly, a user can select a data link by clicking on a heading, a text highlight link, or entries in a table of references and the image viewer 112 automatically navigates to the corresponding image. In some embodiments, an optional overlay is also provided on the image (for example, an anatomical localization overlay, an implant overlay, a measurement overlay, or the like) that outlines, shades, labels, or otherwise highlight an image feature of the image, such as an anatomical structure, measurement, or implanted device. Also, in some embodiments, the matched image feature (or a portion thereof) from the report may be overlaid on the image. For example, the textual language included in a finding or a measurement may be displayed with the linked image so that a user does not need to flip back and forth between the report and the image. For example, information from both the body of the report (for example, the findings section) and the impressions could be displayed together on an image. Combining this data allows a user to see any recommendations that may have been made based on the findings made from a particular image. Also, in some embodiments, default text or data may be added to an image associated with a data link (regardless of whether the text or data is included in the associated report). For example, relevant measurement criteria may be added to an image. As one example, if lung nodule has been identified in an image, displaying the Fleischner criteria may be added to the image to improve a user's confidence in follow-up recommended in the report (or modify the recommendation as needed). Thus, as noted above, the data links, and their automatic creation, simplifies the navigation of images by a user and quickly and accurately shows a user what images and particular image features are being discussed in the report in an unambiguous manner.

For example, the data links may be used to link measurements in a report to the original images from which the measurements were derived. As mentioned previously, it is common in many imaging studies to make measurements during the procedure. These measurements are typically saved as part of the image record. The measurements are also commonly imported in to the reports (manually or automatically whether via DICOM SR, OCR, or the like). However, in the import process, the linkage to the image is not preserved so the user has a list or table of measurements but then the user must look through the images to find each measurement. This is a common task for a cardiologist who is reading an echocardiography study and wants to check the measurements taken by the sonographer for accuracy. The measurements would be extracted by the feature extraction unit 116 (via OCR) from images (screen shots) and included in the table of extracted features table. Accordingly, a user can click on a measurement (or its label) and navigate directly to the relevant images including both the still frame or secondary capture with the measurement and the source multiframe sequence or series from which it was derived so as to ascertain if this is the "best image" and accurate measurement or if they may like to add more measurements as might be done during the creation of the report. As described in more detail below, the automatic linkage described herein may be provided to link to a current imaging study and optionally to prior comparisons including, for example, the identification of optimum comparison studies and images within them.

Similarly, the data links described above may be used to location images associated with qualitative text. For example, by clicking on qualitative text included in a report, the user is automatically taken to the images associated with the text and may highlight the measurements or values associated with the qualitative text.

In some embodiments, if the medical image report is not a document type that supports data links, the medical image report may be converted to a document type that does support data links. For example, the medical image report may be converted to an HTML document, RTF document, PDF document, or the like, which supports data links. In some embodiments, a user may review generated data links and approve or reject links. This user feedback may be used, with one or more machine learning techniques, to improve the natural language processing, features extraction, comparing, generating and insertion of data links, or a combination thereof.

In some embodiments, the data links are used as a lookup into the table containing the image features extracted from an image. Accordingly, when the table containing the extracted image features are stored in a static location, the data links may be preserved even when the report and the images are stored separately from the report (such as in an inaccessible storage location) or subsequently moved to a new location. Also, in some embodiments, the report can be provided with the table of extracted image features so that when the images or the report are exported (for example, on CD, DVD, USB, or the like) that data links between the report and the images are still available and able to be viewed within the typically included viewer in a linked manner or at least navigable by text references in the table (for example, L3 was found in Series 2 images 34-37). Alternatively, in the post processing of the report, thumbnail images with links can be inserted rather than merely a text table.

As described above, in response to a user selecting the data link (such as through the image viewer 112 executed by the user device 106), the linked medical image is displayed to the user. In some embodiments, the image viewer 112 is configured to display both medical image reports as well as images. However, in other embodiments, a separate window (separate from a window displaying the report) may be generated to display the linked medical image. Also, in some embodiments as described above, a feature identified in an image is highlighted when displayed through selection of a data link. For example, an image feature may be highlighted, flashed, labeled, or otherwise marked within an image to further focus the user's attention on the relevant section of the image. Furthermore, selecting a data link may display a plurality of images. For example, an image study may contain multiple views of a medical structure, and, when the electronic processor 108a creates the data link, the data link may reference all the relevant images. When the data link is selected, all of the relevant images may be displayed and the user may scroll or otherwise navigate through the images. Alternatively or in addition, a list of the relevant images may be initially displayed when a user selects the data link and a user can select a relevant image from the list for display. Also, in some embodiments, multiple images may be displayed simultaneously, such as to provide a side-by-side comparison. Such a comparison may be automatically generated or generated by a user selecting images for inclusion in the comparison. Similarly, in some embodiments, one or more rules may be applied to images associated with a selected data link to determine or prioritize the images for display to a user. For example, the rules may define which images or portions of images (or which portions of the medical image report) are more or less relevant to an identified image feature. For example, when a medical image report contains the phrase "tumor shown in sagittal view of brain," the rules may specify that sagittal views of the brain may be displayed before other views of the brain. The rules may be set by a user or may be automatically learned using one or more machine learning techniques. For example, if a reading physician frequently uses a certain view of an organ when reviewing medical image reports, a rule may be generated that prioritizes this view when creating a data link.

It should be understood that the data link may, alternatively or in addition, be inserted into the medical image. Accordingly, when a user views the medical image, the user may be able to select the data link to automatically access the report associated with the medical image, and, in particular, the particular portion of the report referencing the medical image (or an image feature contained therein). Thus, a data link may be used to create a two-way link between a report (a section of a report) and an associated image. As described above for the data link inserted in the medical image report, when a user selects a data link inserted in a medical image, the report may be displayed and a portion of the report may be highlighted to draw the user's attention to the relevant section of the report. When the data link is selected, the electronic processor 108a is configured to display the medical image report (at block 335). For example, when a circled mass is selected, the electronic processor 108a displays portions of the medical image report that reference the mass. In some embodiments, the electronic processor 108a highlights the portions of the medical image report that are relevant to the image feature that was selected.

It should be understood that the method 200 described above may be configured to set the type of image features identified in reports and associated images. For example, the method 200 may be configured to only identify medical structures, only identify particular types of user artifacts, or a combination thereof. Also, the method 200 may be performed or triggered in response to various events. For example, in some embodiments, the report and associated images may be processed as described above in response to a receiving a request from a user to view a report or an image study. Alternatively, due to the computational load of this process, a report and associated images may be processed as described above when the report is stored to the report source 102. Similarly, reports and associated images may be pre-processed according to a predetermined schedule whether for a current study or some rules-based selection of prior comparison studies or based on a triggering event such as an admission of a patient, ordering of a follow up study, or scheduling of an appointment or ingestion of a new imaging study for that patient.

In some embodiments, the electronic processor 115a may access further image studies or other data associated with a patient as part of processing a report for the patient. For example, the electronic processor 115a may access image studies done prior to a current image study to determine if a medical structure or image feature can be found in the prior image studies. Finding relevant medical structures or image features in prior image studies and creating data links to the prior images studies may assist the reading physician in analyzing the medical image report.

For example, since patient demographics are included in a report, this data can be used to link to patient image studies stored in the image study source and a data link may be added to the demographics in the report that allows a user to quickly access these additional studies. Similarly, a data link may be added to a date in the report and a user can select the data links to see all image studies performed on that date (for the patient in question or all patients, for the same imaging modality or all modalities, for the same imaging clinic or all clinics in a network, or a combination thereof). This type of data link may be useful when a patient has a CT head scan and a CT cervical spine scan performed on the same date but they are dictated as separate studies. Similarly, if a report references a follow-up imaging procedure, a data link could be added to this reference that links to the image study generated as part of this recommended follow-up procedure. In addition, if a follow-up image study is not located, one or more alerts may be generated indicating that the follow-up may not have been performed. Accordingly, the linking between image studies may provide unique tracing of recommendations and the follow-ups which could originate either in the currently viewed report or anywhere in the series of reports that constitute the longitudinal record for a patient.

Data links could also be provided to one or more images of prior imaging studies, including when referenced in a "comparisons" section of a report or the body of the report. For example, when a reading physician dictates "On today's exam the mass measures x by y by z, while on the prior study this measured a by b by c," a data link may be added to both measurements that, when selected, display the relevant images used for the measurements. In some embodiments, the relevant images for both measurements may also be displayed for comparison purposes, such as in a side-by-side orientation. Accordingly, the data links described herein may be generated not just to access images within a single image study but provides depth in the longitudinal record (such as for studies occurring within a predetermined window) and the ability to locate a relevant prior image study, open the study for comparison and navigate to the images or other objects, such as the Pressure waveforms or ECG, that are outside of the imaging study that the current report is for. As noted above, the extracted image features are not limited to anatomical structures but may also include descriptions of pathology (disease state or functional pathology). This type of NLP identification and image navigation may require more complex rule sets. For example, a proximal right coronary artery stenosis has a one-to-one text to image relationship. However, some disease states may have a one-to-many text to image relationship or navigation that requires more complex rules. For example, to generate disease-state (pathology) linkages, the systems and methods described above may use a top-level hierarchy that performs a rule-based determination of a simple vs a complex model. The simple model may involve a single modality (for example, an echo US) and a simple disease state. For example, when the report text includes the phrase "Aortic Stenosis," the systems and methods described above may select a modality, an image, and an image filter for measurements, wherein the modality associated with the report from which the text was retrieve is selected, the images to display include the Parasternal Short Axis (PSAX) image, which provides a best view to visualize valve anatomy, the Parasternal Long Axis (PLAX) image, which provides a best view to visualize valve motion, and a Continuous wave (CW) Doppler image of the aortic valve, which is best to evaluate function. With these proper image selections, the measurements associated with these selected images are considered the relevant measurements. Accordingly, with these selections, when a user selects "Aortic Value Mean Gradient" measurement in the report, the CW Doppler image is displayed. Similarly, if the user selects the "Aortic Valve Peak Velocity" measurement in the report, the PLAX and CW Doppler images are displayed.

In contrast, the complex model may handle multiple modalities and situations where the disease state is not linked to solely one structure. In this model, additional levels of organization may be employed. Also, due to the number of images that may be associated with the disease state, a priority order may be employed. For example, the complex model may be used to select a primary modality (modality associated with the report from which the text is selected), a primary modality image selection, a primary Image filter for measurements, and a priority ordering of images. The model may also make similar selections for a secondary modality selection, a third modality selection, and the like. For example, when a report includes the text "Hypertrophic cardiomyopathy (HCM)," the complex model may select the following echo images (as the primary modality) in the following order to display: Parasternal long axis (PLAX) with 2D measurements, Parasternal short axis (PSAX) with 2D measurements, Left ventricle strain rate curve, Mitral valve Doppler with measurements. Tissue Doppler with measurements, Pulmonary vein Doppler with measurements, and Continuous Wave Doppler (CW) of tricuspid valve with measurements. Similarly, the complex model may select the following cardiac MR images (as the secondary modality) in the following order to display: four chamber end diastolic view with and without contrast.

It should be understood that although the previous examples select a measurement to associate with the data link, such a measurement is optional. For example, some disease states may not be associated with a specific measurement although they may be associated with a particular anatomical structure.

Thus, embodiments of the invention provide methods and systems for automatically linking entries in a medical image report to an image. It should be understood that while embodiments described herein are directed towards medical image reports, the methods and systems may be applied to other types of documents, including, for example, operative reports and clinical procedure notes. Similarly, videos, audio recordings, or a combination thereof may be processed to extract image features that can be linked to a corresponding report or image as described above.

Various features and advantages of the invention are set forth in the following claims.

What is claimed is:

1. A method for automatically linking entries in a medical image report to at least one image of a medical image study associated with the medical image report, the method comprising:
   identifying, with at least one electronic processor, a first plurality of image features referenced in text included in the medical image report using natural language processing;
   identifying, with the at least one electronic processor, a second plurality of image features in images included in the medical image study;
   comparing, with the at least one electronic processor, the first plurality of image features and the second plurality of image features; and
   in response to a first image feature included in the first plurality of image features and a second image feature included in the second plurality of image features matching,
   creating, with the at least one electronic processor, a data link between the medical image report and an image included in the medical image study including the second image feature, wherein creating the data link includes generating a first table including the first plurality of image features and a second table including the second plurality of image features, and wherein the data link is used as a lookup into at least one of the first table and the second table, and
   automatically inserting, with the at least one electronic processor, the data link into the medical image report, the data link being selectable by a user to display the image.

2. The method of claim 1, wherein at least one of the first plurality of image features includes at least one selected from a group consisting of an anatomical structure, a description of pathology, a surgical feature, a medical device, and a medical implant.

3. The method of claim 1, wherein at least one of the second plurality of image features includes a user artifact.

4. The method of claim 1, further comprising converting, with the at least one electronic processor, the medical image report to a document format supporting usage of the data link before inserting the data link.

5. The method of claim 1, wherein the data link is inserted at a location where the first image feature was identified in the medical image report.

6. The method of claim 1, wherein creating the data link includes creating a data link between a plurality of images included in the medical image study and the medical image report, wherein each of the plurality of images includes an image feature matching the first image feature.

7. The method of claim 1, wherein identifying the second plurality of image features includes identifying the second plurality of image features using multi-atlas image segmentation.

8. The method of claim 1, wherein identifying the first plurality of image features includes identifying the first plurality of image features in response to the medical image report being submitted to a report source.

9. The method of claim 1, further comprising generating an overlay for the image, wherein the overlay highlights the second image feature in the image.

10. The method of claim 1, further comprising generating an overlay for the image based on the data link, wherein the overlay includes text based on the first image feature identified in the medical image report.

11. The method of claim 1, further comprising
   identifying a third plurality of image features in images included in a second medical image study;
   comparing the first plurality of image features and the third plurality of image features; and
   in response to a third image feature included in the first plurality of image features and a fourth image feature included in the third plurality of image features matching
   creating, with the at least one electronic processor, a second data link between the medical image report and a second image included in the second medical image study including the fourth image feature, and
   automatically inserting, with the at least one electronic processor, the second data link into the medical image report, the data link being selectable by the user to display the second image.

12. The method of claim 11, wherein identifying the third plurality of image features includes identifying the third plurality of image features in images included in a prior medical image study for a patient associated with the first medical image study.

13. A system for automatically linking entries in a medical image report to at least one image of a medical image study associated with the medical image report, the system comprising:
   at least one electronic processor configured to:
   identify a first plurality of image features referenced in text included in the medical image report using natural language processing,
   identify a second plurality of image features in images included in the medical image study,
   compare the first plurality of image features and the second plurality of image features, and in response to a first image feature included in the first plurality of image features and a second image feature included in the second plurality of image features matching, create a data link between the medical image report and an image included in the medical image study including the second image feature, wherein creating the data link includes generating a first table including the first plurality of image features and a second table including the second plurality of image features, and wherein the data link is used as a lookup into at least one of the first table and the second table, and automatically insert the data link into the image in the medical image study, wherein the data link is selectable to display the medical image report.

14. The system of claim 13, wherein the at least one electronic processor is configured to insert the data link into the image at a portion of the image containing the second image feature.

15. The system of claim 13, wherein at least one of the second plurality of image features includes a user artifact.

16. Non-transitory, computer-readable medium storing instructions that, when executed by at least one electronic processor, cause the at least one electronic processor to perform a set of functions, the set of functions comprising:

identifying a first plurality of annotations referenced in text included in a medical image report using natural language processing, identifying a second plurality of annotations in images included in a medical image study associated with the medical image report, comparing the first plurality of annotations and the second plurality of annotations, and in response to a first annotation included in the first plurality of annotations and a second annotation included in the second plurality of annotations matching, creating a data link between the medical image report an image included in the medical image study including the second annotation, wherein creating the data link includes generating a first table including the first plurality of image features and a second table including the second plurality of image features, and wherein the data link is used as a lookup into at least one of the first table and the second table, and inserting the data link into the medical image report, the data link selectable to display the image.

17. The non-transitory, computer-readable medium of claim 16, wherein identifying the second plurality of annotations includes generating a table storing an identifier of each of the second plurality of annotations and an identifier of an image included in the medical image study including each annotation, and wherein the data link is used as a lookup into the table to display the image.

18. The non-transitory, computer-readable medium of claim 16, wherein identifying the second plurality of annotations includes analyzing a saved screenshot of the image to identify a measurement.

* * * * *